United States Patent [19]

Davies

[11] Patent Number: 4,782,824
[45] Date of Patent: Nov. 8, 1988

[54] EXTERNAL AIRWAY SUPPORT

[76] Inventor: Gerald G. Davies, 403 Magowan Ave., Iowa City, Iowa 52240

[21] Appl. No.: 76,790

[22] Filed: Jul. 23, 1987

[51] Int. Cl.⁴ .............................................. A61F 5/01
[52] U.S. Cl. ................................ 128/76 R; 128/25 R
[58] Field of Search ............... 128/68, 76 R, 75, 24 R, 128/25 R

[56] References Cited

U.S. PATENT DOCUMENTS

| | | | |
|---|---|---|---|
| 3,313,297 | 4/1967 | Applegate et al. | 128/75 |
| 3,724,452 | 4/1973 | Nitschke | 128/75 |
| 4,643,174 | 2/1987 | Horiuchi | 128/76 R |

Primary Examiner—Edgar S. Burr
Assistant Examiner—Moshe I. Cohen
Attorney, Agent, or Firm—Richard O. Gray, Jr.

[57] ABSTRACT

There is disclosed a device to be worn by a human patient for maintaining the upper airway passage of the patient in an open, unobstructed position. The device includes a lower portion arranged to rest upon the upper thorax of the patient and an upper portion connected to and braced by the lower portion. The upper portion includes means for lifting the lower jaw of the patient and thrusting the lower jaw of the patient forward. A posterior portion connected to the lower and upper portions maintains the positioning of the lower and upper portions and prevents backward movement of the patient's lower jaw.

15 Claims, 4 Drawing Sheets

EXTERNAL AIRWAY SUPPORT

BACKGROUND OF THE INVENTION

The present invention is directed to a device to be worn by a human patient and more particularly to an external airway support to alleviate the airway obstruction of unconsciousness that may occur in a wide variety of circumstances such as sleep apnea, emergency treatment and transport of unconscious individuals and where sedation or anesthesia is employed.

Airway obstruction can occur in human beings during states of unconsciousness which can occur with natural sleep, as in sleep apnea, and with conditions of pathologically or pharmacologically produced decreases in consciousness. It is believed that there is a common mechanism underlying the airway occlusion in these circumstances. The obstruction is caused by a decrease in tone of the muscles of the pharynx, mandible (lower jaw) and neck. The overall effect of this decrease in muscle tone is a collapsing inward, and hence narrowing, of the upper airway. The most critical change, which can cause total airway obstruction, is the falling back of the tongue to occupy the pharyngeal air passage. This critical obstruction is believed to be caused by a decrease in the activity of the genioglossus muscle which connects the tongue to the point of the chin. This is most likely the cause of the common phenomenon of snoring as well as the potentially life threatening airway obstruction of sleep apnea.

Anesthesiologists are well aware of the problem of airway obstruction of unconscious patients as it invariably accompanies general anesthesia. Prior to the instant invention, the problem has been managed by manually lifting the lower jaw with slight extension of the head on the neck. This has the effect of lifting the tongue from the posterior pharyngeal wall to restore unobstruction of the airway.

The present invention will be of great value to the anesthesiologist in anesthesia practice since it can be used to maintain an unobstructed airway passage of the patient while freeing the anesthesiologist from the necessity of manually administering suitable treatment. It could be used to free the anesthesiologist's hands during the management of most spontaneously breathing non-intubated patients undergoing general anesthesia or sedation. It could also be used to allow airway maintenance in situations where manual airway support is impractical. Such situations can include surgery which is performed in the area of the patients head under heavy sedation, such as, for example in eye surgery or neurosurgery.

There are many other circumstances wherein the upper airway passage of a patient could become obstructed. For example, many, if not most, hospitalized patients receive sedation at one time or another. Sedation combined with debility can frequently lead to airway obstruction. Many cases of cardiac arrest in hospitals can be traced to this problem. These patients can be recognized by appearing asleep, head slumped unsupported, with mouth ajar and snoring. Another circumstance is in the emergency transport of unconscious individuals encountered by, for example, ambulance personnel wherein the unconsciousness of the individual being transported could cause an airway obstruction. Lastly, sleep apnea has been estimated as afflicting between 1 and 3% of the population. Very often it is of the obstructive type directly analogous to the problem seen in anesthesia and sedation wherein an obstruction in the upper air passage occurs due to loss of muscle tone with the onset of sleep.

Unfortunately, current treatments of sleep apnea and other forms of airway obstruction have included tracheostomy and a variety of major surgical modifications of the upper airway. A common conservative treatment has also been the use of a positive pressure breathing mask.

Hence, as can be seen from the above, there is a need in the art for an externally applied airway support to prevent obstruction of the upper airway passage in patients due to the onset of sleep or unconsciousness. Such a device must be simple, cost effective, and conservative in treatment to promote wide spread patient acceptability.

SUMMARY OF THE INVENTION

The invention provides a device to be worn by a human patient for maintaining the upper airway of the patient in an open, unobstructed position. The device includes a lower portion arranged to rest upon the upper thorax of the patient and an upper portion connected to and braced by the lower portion. The upper portion includes means for lifting the lower jaw of the patient and thrusting the lowered jaw of the patient forward. The device further includes a posterior portion connected to the lower and upper portions. The posterior portion is arranged to maintain the positioning of the lower and upper portions.

Preferably, the lower and upper portions are arranged to encircle the anterior portion of the patient's neck and are joined together at connection points on opposite sides of the patient's neck. The device also preferably includes hinge means at the connection points to render the angular position between the lower and upper portions adjustable.

The upper portion of the device preferably includes a substantially lateral portion and a pair of flange portions extending from opposite ends of the lateral portion and terminating at the connection points. Preferably, the lateral portion and the flange portions are joined at a location adapted to be in the vicinity of the patient's lower jaw rami with the upper portion further including a pair of lower jaw rami supports for supporting the lower jaw rami of the patient.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings wherein like reference numerals identify identical elements, and wherein:

DETAILED DESCRIPTION

Figure 1:
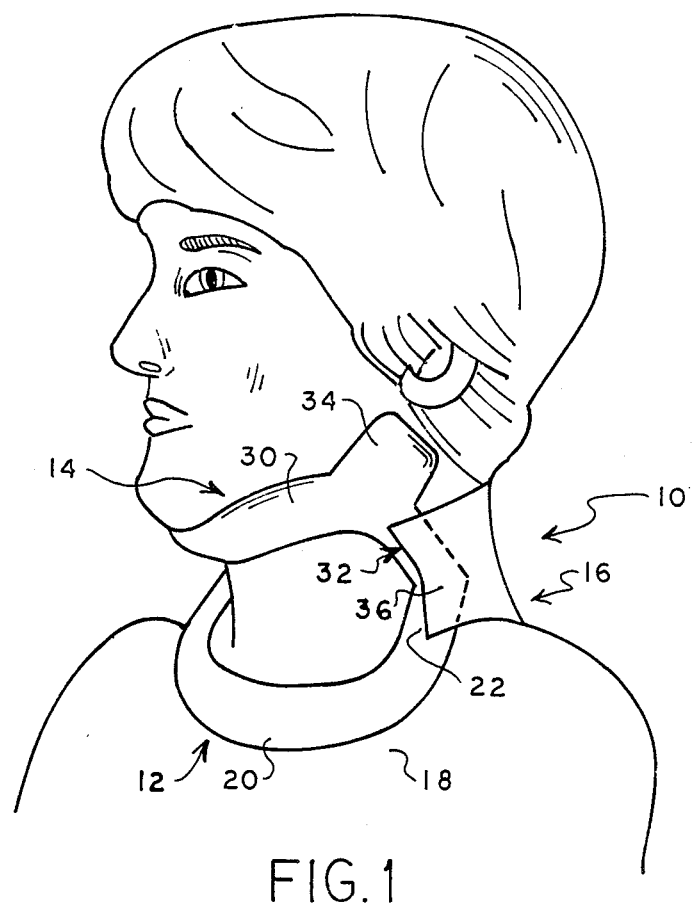
FIG. 1 is a perspective view illustrating an external airway support embodying the present invention being worn by a human patient.

Referring now to FIG. 1, it illustrates an external airway support 10 embodying the present invention being worn by a human patient. The external airway support 10 generally includes a lower portion 12, an upper portion 14, and a posterior portion 16.

The lower portion 12 is arranged to rest upon the upper thorax 18 of the patient and includes a generally lateral portion 20 which terminates in a pair of upstanding flange portions, one of which can be seen at 22.

The upper portion 14 includes a generally lateral portion 30 and a pair of downwardly turned flange portions, one of which can be seen at 32. The lateral portion 30 and the flange portions 32 are joined at a location adapted to be in the vicinity of the patient's lower jaw rami. To support the lower jaw rami of the patient, the upper portion 14 also includes a pair of lower jaw rami supports, one of which can be seen at 34. Preferably, the lower jaw rami supports 34 are located on the upper portion 14 at the connection of the lateral portion 30 with the flange portions 32.

The upper portion 14 and lower portion 12 are connected together by the flanges 32 and 22 at connection points 36. In accordance with this preferred embodiment, the upper portion 14 and lower portion 12 are integrally formed together. As can be further seen in FIG. 1, the lower and upper portions 12 and 14 are arranged to encircle the anterior portion of the patient's neck and the connection points 36 are located on opposite sides of the patient's neck.

The posterior portion 16 encircles the posterior of the patient's neck and is connected to the lower and upper portions 12 and 14. The posterior portion 16 maintains the positioning of the lower and upper portions 12 and 14 and prevents backward movement of the patient's mandible or lower jaw as illustrated. The posterior portion 16 can be connected to the lower and upper portions 12 and 14 in the vicinity of the connection points 36 by a hook and pile which is best seen at 40 in FIG. 3.

In operation, the lower portion 12 of the external airway support 10 is arranged to rest upon the upper thorax of the patient. The upper portion 14 is braced by the lower portion 12 and together, they extend around and encircle the anterior portion of the patient's neck. the upper portion 14 engages the patient's mandible or lower jaw at the lower jaw rami, along the jaw bone, and under the chin while the posterior portion 16 maintains the positioning of the lower and upper portions on the patient as illustrated. As a result, the upper portion 14 lifts the lower jaw of the patient and thrusts the lower jaw of the patient forward. This precludes the obstruction of the patient's upper airway not withstanding the onset of sleep or unconsciousness.

Figure 2:
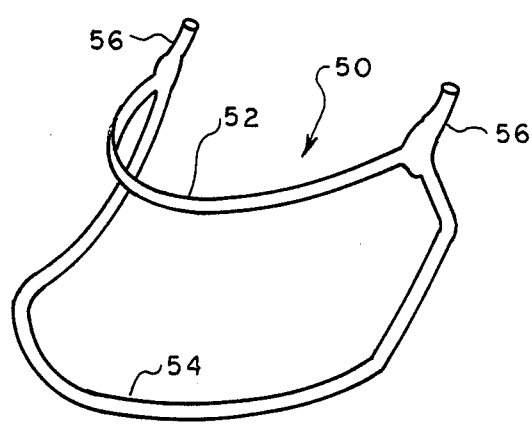
FIG. 2 is a perspective view of a metallic frame which can be utilized in making the lower and upper portions of the external airway support illustrated in FIG. 1.

Referring now to FIG. 2, it illustrates in perspective view a frame 50 which can be utilized to form the foundation of the integral structure including the lower portion 12, upper portion 14, and rami supports of the external airway support illustrated in FIG. 1. The frame 50 is preferably constructed of steel and perferably a resilient malleable steel material of for example 4 mm. in diameter. The frame is shaped to form an upper ellipse 52 to form the basis of the upper portion which supports the mandible or lower jaw and a lower ellipse 54 which forms the basis of the lower portion which rests against the patient's upper thorax. The frame 50 includes additional projections 56 which correspond in position to the angles of the patient's jaw and which are utilized for forming the basis of the rami supports. The frame 50, once formed to the proper shape, is subsequently provided with medium density polyurethane foam to form comfortable contact points with the patient's body.

Figure 3:
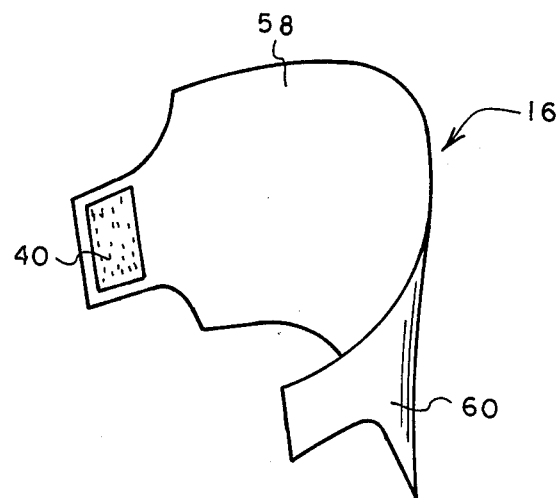
FIG. 3 is a perspective view of the posterior portion of the external airway support illustrated in FIG. 1.

Referring now to FIG. 3, it illustrates the posterior portion of the external airway support in greater detail. As previously explained, the posterior portion 16 holds the lower and upper portions in position and prevents backward movement of the mandible or lower jaw. To that end, it can be seen that the posterior portion 16 includes an upper neck extension 58 and a lower extension 60. The extensions 58 and 60 preclude backward movement of the patient's head and thus backward movement of the upper support which otherwise might occur when the patient is placed into a reclining position. As also can be seen in FIG. 3, the posterior portion includes the hook and pile 40 which is utilized to connect the posterior portion to the lower and upper portions of the external airway support.

Figure 4:
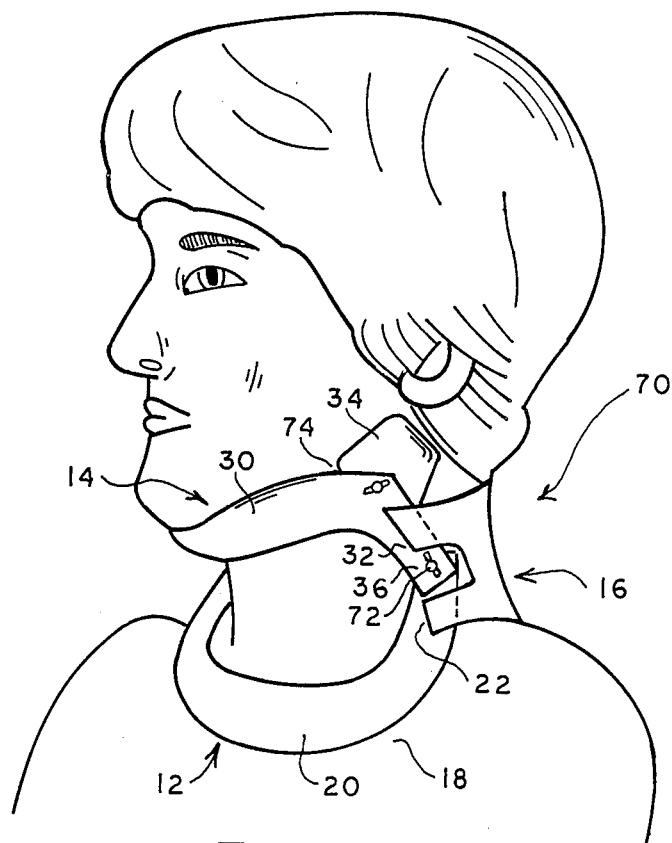
FIG. 4 is a perspective view similar to FIG. 1 illustrating another external airway support embodying the present invention being worn by a human patient.

Referring now to FIG. 4, it illustrates another external airway support 70 embodying the present invention. Because the external airway support 70 illustrated in FIG. 4 is similar to the external airway support 10 illustrated in FIG. 1, those elements which it has in common therewith have been given identical reference characters.

The external airway support 70 illustrated in FIG. 4 is constructed so that the lower portion 12 and upper portion 14 are separately formed. Both the lower portion 12 and upper portion 14 can be formed from plastic, for example, along with the posterior portion 16. The lower portion 12 and upper portion 14 are pivotal about a hinged connection formed by a wing nut 72 to render the position between the lower and upper portions adjustable. To maintain a desired angular position between the lower and upper portions, the wing nut 72 can be provided with ratchetted contacts. Because the lower and upper portions are adjustable with respect to one another, the amount of support given to the lower jaw can be tailored for an individual patient by the adjustment of the angle between the lower and upper portions.

The rami supports 34 of the external airway support 70 are padded and formed in the shape of eccentric cams which are attached off center on the inside of the upper portion 14 by small wing nuts 74. By rotating the rami supports in an upward direction the forward pressure on the patient's rami of the lower jaw will be increased and the rami supports will also come into closer contact with the underside of the angle of the mandible or lower jaw. This provides an adjustable support for the patient's lower jaw rami.

The posterior portion 16 of the external airway support 70 can be identical to the posterior portion of the external airway support 10 illustrated in FIG. 1. Again, it can be attached to the lower and upper portions by hook and pile and prevents the upper portion which supports the patient's lower jaw from moving backward.

From the foregoing, it can be seen that the present invention provides an external airway support device to be worn by a human patient for maintaining the upper airway of the patient in an open, unobstructed position. The external airway support of the present invention is useful in the prevention of upper airway obstruction associated with sleep apnea, anesthesia, sedation, and debility. Because the device is simple to use, it could be used in the home to prevent snoring and obstructive sleep apnea. The external airway support also of course finds particular application in the hospital environment for use in operating rooms, emergency rooms, and general wards. It could also be useful in the emergency rescue and transport, by paramedical personnel, of patients with decreased levels of consciousness.

I claim:

1. A device to be worn by a human patient for maintaining the upper airway of the patient in an open, unobstructed position, said device comprising:
   a lower portion arranged to rest upon the upper thorax of the patient;
   an upper portion connected to and braced by said lower portion, said upper portion including means for lifting the lower jaw of the patient and a pair of lower jaw rami supports for thrusting the lower jaw of the patient forward; and
   a posterior portion connected to said lower and upper portions, said posterior portion being arranged to maintain the positioning of said lower and upper portions.

2. A device as defined in claim 1 wherein said lower and upper portions are integrally formed together.

3. A device as defined in claim 1 wherein said lower and upper portions are separately formed.

4. A device as defined in claim 3 further including means for providing angular adjustment of said lower and upper portions.

5. A device as defined in claim 1 wherein said lower and upper portions are arranged to encircle the anterior portion of the patient's neck.

6. A device as defined in claim 5 wherein said lower and upper portions are joined together at connection points on opposite sides of the patient's neck.

7. A device as defined in claim 5 wherein said lower and upper portions are integrally formed together.

8. A device as defined in claim 6 further including hinge means at said connection points to render the angular position between said lower and upper portions adjustable.

9. A device as defined in claim 5 wherein said posterior portion is arranged to encircle the patient's posterior neck portion.

10. A device as defined in claim 9 further including hook and pile for connecting said posterior portion to said lower and upper portions.

11. A device as defined in claim 9 wherein said posterior portion includes means for preventing backward movement of the patient's head.

12. A device as defined in claim 6 wherein said upper portion includes a substantially lateral portion and a pair of flange portions extending from opposite ends of said lateral portion and terminating at said connection points.

13. A device as defined in claim 12 wherein said lateral portion and said flange portions are joined at a location adapted to be in the vicinity of the patient's lower jaw rami.

14. A device as defined in claim 13 wherein said lower jaw rami supports are located on said upper portion at the connection of said interal portion with said flange portions.

15. A device as defined in claim 14 wherein said lower jaw rami supports are adjustable on said upper portion.

* * * * *